(12) United States Patent
Raciti et al.

(10) Patent No.: US 11,791,035 B2
(45) Date of Patent: Oct. 17, 2023

(54) SYSTEMS AND METHODS FOR ARTIFICIAL INTELLIGENCE POWERED MOLECULAR WORKFLOW VERIFYING SLIDE AND BLOCK QUALITY FOR TESTING

(71) Applicant: PAIGE.AI, Inc., New York, NY (US)

(72) Inventors: Patricia Raciti, New York, NY (US); Christopher Kanan, Pittsford, NY (US); Alican Bozkurt, New York, NY (US); Belma Dogdas, Ridgewood, NJ (US)

(73) Assignee: Paige.AI, Inc., New York, NY (US)

(*) Notice: Subject to any disclaimer, the term of this patent is extended or adjusted under 35 U.S.C. 154(b) by 0 days.

(21) Appl. No.: 17/539,664

(22) Filed: Dec. 1, 2021

(65) Prior Publication Data

US 2022/0293248 A1 Sep. 15, 2022

Related U.S. Application Data

(60) Provisional application No. 63/158,781, filed on Mar. 9, 2021.

(51) Int. Cl.
*G06K 9/00* (2022.01)
*G16H 30/40* (2018.01)
(Continued)

(52) U.S. Cl.
CPC ............. *G16H 30/40* (2018.01); *G06N 20/00* (2019.01); *G06T 7/0014* (2013.01); *G16H 50/20* (2018.01); *G16H 70/60* (2018.01)

(58) Field of Classification Search
CPC ........ G16H 30/40; G16H 50/20; G16H 70/60; G06N 20/00; G06T 7/0014
See application file for complete search history.

(56) References Cited

U.S. PATENT DOCUMENTS

| 10,731,223 B2 | 8/2020 | Kennedy et al. |
| 2018/0226138 A1* | 8/2018 | Leavitt ............. G01N 35/00871 |

(Continued)

FOREIGN PATENT DOCUMENTS

| CN | 108538399 A | * | 9/2018 | |
| CN | 113454733 A | * | 9/2021 | ........... G06F 3/0482 |

(Continued)

OTHER PUBLICATIONS

International Search Report and Written Opinion issued in International Application No. PCT/US2021/062092, dated Mar. 25, 2022 (15 pages).

*Primary Examiner* — Xin Jia
(74) *Attorney, Agent, or Firm* — Bookoff McAndrews, PLLC

(57) ABSTRACT

Systems and methods are disclosed for verifying slide and block quality for testing. The method may comprise receiving a collection of one or more digital images at a digital storage device. The collection may be associated with a tissue block and corresponding to an instance. The method may comprise applying a machine learning model to the collection to identify a presence or an absence of an attribute, determining an amount or a percentage of tissue with the attribute from a digital image in the collection that indicates the presence of the attribute, and outputting a quality score corresponding to the determined amount or percentage.

20 Claims, 10 Drawing Sheets

(51) Int. Cl.
*G16H 70/60* (2018.01)
*G16H 50/20* (2018.01)
*G06N 20/00* (2019.01)
*G06T 7/00* (2017.01)

(56) References Cited

U.S. PATENT DOCUMENTS

| | | |
|---|---|---|
| 2019/0164287 A1 | 5/2019 | Gregson et al. |
| 2021/0090694 A1 | 3/2021 | Colley et al. |
| 2021/0166381 A1* | 6/2021 | Yip .................. G06K 9/6271 |
| 2021/0166785 A1 | 6/2021 | Yip et al. |
| 2021/0263055 A1* | 8/2021 | Mitra ............... G01N 35/00613 |

FOREIGN PATENT DOCUMENTS

| | | | |
|---|---|---|---|
| JP | 2016533819 A | * | 11/2016 |
| WO | 2020243193 A1 | | 3/2020 |
| WO | 2020243550 A1 | | 3/2020 |

* cited by examiner

SYSTEMS AND METHODS FOR ARTIFICIAL INTELLIGENCE POWERED MOLECULAR WORKFLOW VERIFYING SLIDE AND BLOCK QUALITY FOR TESTING

RELATED APPLICATION(S)

This application claims priority to U.S. Provisional Application No. 63/158,781 filed Mar. 9, 2021, the entire disclosure of which is hereby incorporated herein by reference in its entirety.

FIELD OF THE DISCLOSURE

Various embodiments of the present disclosure pertain generally to image processing methods. More specifically, particular embodiments of the present disclosure relate to systems and methods for verifying slide and block quality for testing.

BACKGROUND

Today's workflow for genomic sequencing of a tumor has many inefficiencies. For example, current workflow processes often require a pathologist to re-review materials to select the best slides or sections of tumor areas for sequencing, which may be challenging and time consuming.

Difficulties in current techniques include identifying the best tissue block and/or slides taken from a human or veterinary patient for testing (e.g., genomic sequencing), as well as verifying that the chosen tissue block and/or slides taken from a patient contain adequate tumor tissue.

The background description provided herein is for the purpose of generally presenting the context of the disclosure. Unless otherwise indicated herein, the materials described in this section are not prior art to the claims in this application and are not admitted to be prior art, or suggestions of the prior art, by inclusion in this section.

SUMMARY

According to certain aspects of the present disclosure, systems and methods are disclosed for verifying slide and block quality for testing.

A method for verifying slide and block quality for testing may be computer-implemented. The method may include receiving a collection of one or more digital images at a digital storage device. The collection may be associated with a tissue block and corresponding to an instance. The method may include applying a machine learning model to the collection to identify a presence or an absence of an attribute, determining an amount or a percentage of tissue with the attribute from a digital image in the collection that indicates the presence of the attribute, and outputting a quality score corresponding to the determined amount or percentage.

Determining the amount or percentage may include summing and normalizing the digital image in the collection that indicates the presence of the attribute by a total amount of tissue. The digital image may be a digital histopathology image.

The method may include partitioning each digital image of the collection of digital images into a collection of tiles, detecting and/or segmenting a tissue region from a background of the digital image to create a tissue mask, and removing all tiles in the collection of tiles that comprise the background. Detecting and/or segmenting may include using one or more thresholding-based methods and running a connected components algorithm. Detecting and/or segmenting may include using one or more segmentation algorithms.

The method may include determining a tissue block with a highest quality score for subsequent testing. The method may include indicating to a user that the tissue block has at least one additional slide to prepare for testing. The method may include determining whether the quality score may be sufficiently low. The method may include indicating to a user to prepare a new block for testing when the quality score may be determined to be sufficiently low.

The method may include outputting a function of at least one variable corresponding to the quality score. The function of the at least one variable may be a linear function. The function of the at least one variable may be a nonlinear function.

The method may include outputting a binary image indicating where the attribute may be located. The method may include receiving a synoptic annotation. The synoptic annotation may include one or more label for each digital image. The one or more label may be a pixel-level label, a tile level label, a slide-level label, and/or a part specimen-level label.

A system for using a machine learning model to verify slide and block quality for testing may include at least one memory storing instructions and at least one processor configured to execute the instructions to perform operations. The operations may include receiving a collection of one or more digital images at a digital storage device. The collection may be associated with a tissue block and corresponding to an instance. The operations may include applying a machine learning model to the collection to identify a presence or an absence of an attribute, determining an amount or a percentage of tissue with the attribute from a digital image in the collection that indicates the presence of the attribute, and outputting a quality score corresponding to the determined amount or percentage.

Determining the amount or percentage may include summing and normalizing the digital image in the collection that indicates the presence of the attribute by a total amount of tissue.

A non-transitory computer-readable medium may store instructions that, when executed by a processor, perform a method of using a machine learning model to verify slide and block quality for testing. The method may include receiving a collection of one or more digital images at a digital storage device. The collection may be associated with a tissue block and corresponding to an instance. The method may include applying a machine learning model to the collection to identify a presence or an absence of an attribute, determining an amount or a percentage of tissue with the attribute from a digital image in the collection that indicates the presence of the attribute, and outputting a quality score corresponding to the determined amount or percentage.

The method may further include partitioning each digital image of the collection of digital images into a collection of tiles, detecting and/or segmenting a tissue region from a background of the digital image to create a tissue mask, and removing all tiles in the collection of tiles that comprise the background.

It is to be understood that both the foregoing description and the following detailed description are exemplary and explanatory only, and are not restrictive of the disclosed embodiments.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

DESCRIPTION OF THE EMBODIMENTS

Figure 1A:
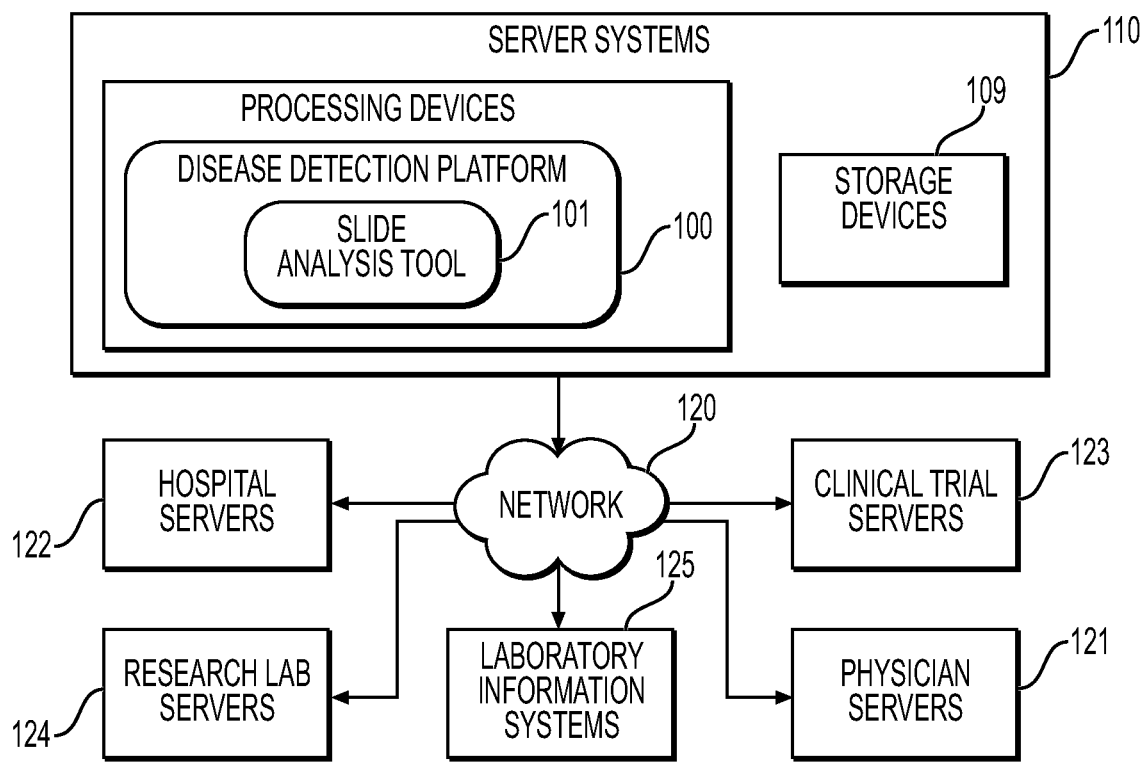
FIG. 1A illustrates an exemplary block diagram of a system and network for verifying slide and block quality for testing, according to an exemplary embodiment of the present disclosure.

Reference will now be made in detail to the exemplary embodiments of the present disclosure, examples of which are illustrated in the accompanying drawings. Wherever possible, the same reference numbers will be used throughout the drawings to refer to the same or like parts.

The systems, devices, and methods disclosed herein are described in detail by way of examples and with reference to the figures. The examples discussed herein are examples only and are provided to assist in the explanation of the apparatuses, devices, systems, and methods described herein. None of the features or components shown in the drawings or discussed below should be taken as mandatory for any specific implementation of any of these devices, systems, or methods unless specifically designated as mandatory.

Also, for any methods described, regardless of whether the method is described in conjunction with a flow diagram, it should be understood that unless otherwise specified or required by context, any explicit or implicit ordering of steps performed in the execution of a method does not imply that those steps must be performed in the order presented but instead may be performed in a different order or in parallel.

As used herein, the term "exemplary" is used in the sense of "example," rather than "ideal." Moreover, the terms "a" and "an" herein do not denote a limitation of quantity, but rather denote the presence of one or more of the referenced items.

Techniques discussed herein may use AI technology to identify a best tissue block, and/or slides for testing, and may verify that the chosen tissue block and/or slides taken from a patient contain adequate volume/mass of tumor. Data and predictions may be aggregated and made available instantaneously via any user interface (e.g. through a digital pathology viewing system, report, or laboratory information system, etc.). Machine learning algorithms may rapidly and simultaneously assess for adequacy, categorize the sample into diagnostic categories, and screen for the most likely molecular changes, limiting the total molecular testing performed on a tumor and therefore, increasing the likelihood of a valid molecular result due to sufficient quantities of tumor.

FIG. 1A illustrates a block diagram of a system and network for verifying slide and block quality, using machine learning, according to an exemplary embodiment of the present disclosure.

Specifically, FIG. 1A illustrates an electronic network 120 that may be connected to servers at hospitals, laboratories, and/or doctors' offices, etc. For example, physician servers 121, hospital servers 122, clinical trial servers 123, research lab servers 124, and/or laboratory information systems 125, etc., may each be connected to an electronic network 120, such as the Internet, through one or more computers, servers, and/or handheld mobile devices. According to an exemplary embodiment of the present application, the electronic network 120 may also be connected to server systems 110, which may include processing devices that are configured to implement a disease detection platform 100, which includes a slide analysis tool 101 for analyzing tissues in a WSI, according to an exemplary embodiment of the present disclosure.

The physician servers 121, hospital servers 122, clinical trial servers 123, research lab servers 124, and/or laboratory information systems 125 may create or otherwise obtain images of one or more patients' cytology specimen(s), histopathology specimen(s), slide(s) of the cytology specimen(s), digitized images of the slide(s) of the histopathology specimen(s), or any combination thereof. The physician servers 121, hospital servers 122, clinical trial servers 123, research lab servers 124, and/or laboratory information systems 125 may also obtain any combination of patient-specific information, such as age, medical history, cancer treatment history, family history, past biopsy or cytology information, etc. The physician servers 121, hospital servers 122, clinical trial servers 123, research lab servers 124, and/or laboratory information systems 125 may transmit digitized slide images and/or patient-specific information to server systems 110 over the electronic network 120. Server systems 110 may include one or more storage devices 109 for storing images and data received from at least one of the physician servers 121, hospital servers 122, clinical trial servers 123, research lab servers 124, and/or laboratory information systems 125. Server systems 110 may also include processing devices for processing images and data stored in the one or more storage devices 109. Server systems 110 may further include one or more machine learning tool(s) or capabilities. For example, the processing devices may include a machine learning tool for a disease detection platform 100, according to one embodiment. Alternatively or in addition, the present disclosure (or portions of the system and methods of the present disclosure) may be performed on a local processing device (e.g., a laptop).

The physician servers 121, hospital servers 122, clinical trial servers 123, research lab servers 124, and/or laboratory information systems 125 refer to systems used by pathologists for reviewing the images of the slides. In hospital settings, tissue type information may be stored in a laboratory information systems 125. According to an exemplary embodiment of the present disclosure, cells in a WSI that share similar targets may be grouped without needing to access the laboratory information systems 125. Additionally, access to laboratory information systems content may be limited due to its sensitive content.

Figure 1B:
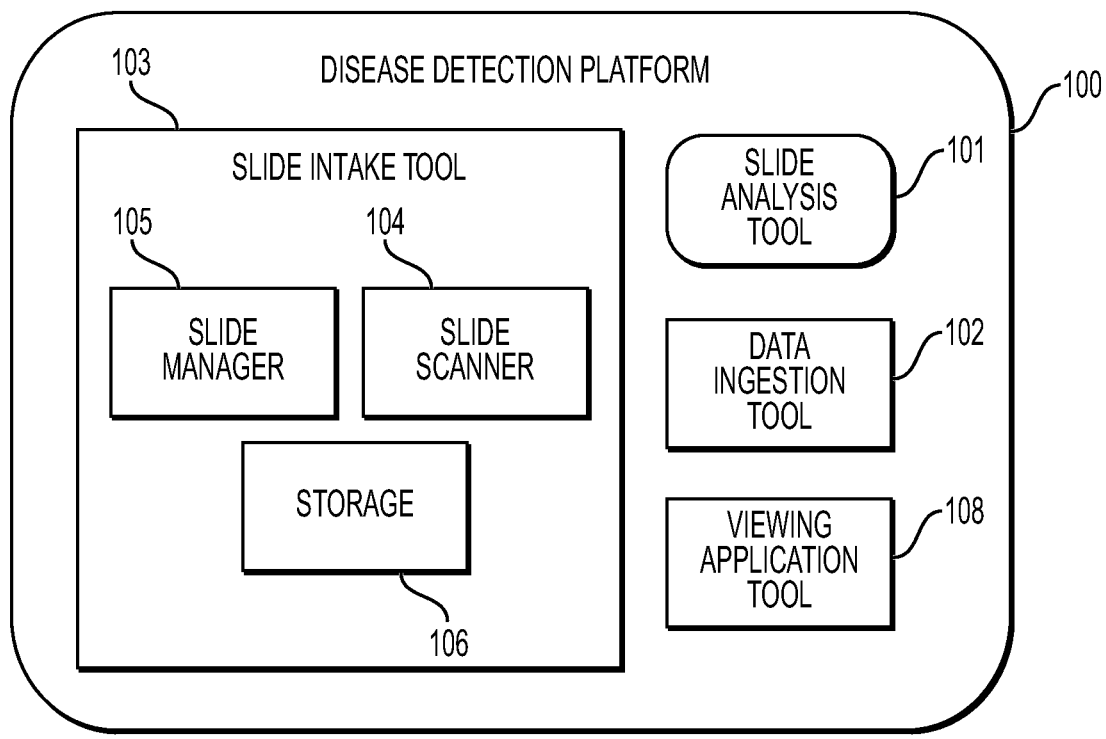
FIG. 1B illustrates an exemplary block diagram of a disease detection platform, according to an exemplary embodiment of the present disclosure.

FIG. 1B illustrates an exemplary block diagram of a disease detection platform 100 for verifying slide and block quality, using machine learning.

Specifically, FIG. 1B depicts components of the disease detection platform 100, according to one embodiment. For example, the disease detection platform 100 may include a slide analysis tool 101, a data ingestion tool 102, a slide intake tool 103, a slide scanner 104, a slide manager 105, a storage 106, and a viewing application tool 108.

The slide analysis tool 101, as described below, refers to a process and system for grouping cells in a WSI that share similar targets, according to an exemplary embodiment.

The data ingestion tool 102 refers to a process and system for facilitating a transfer of the digital pathology images to the various tools, modules, components, and devices that are used for classifying and processing the digital pathology images, according to an exemplary embodiment.

The slide intake tool 103 refers to a process and system for scanning pathology images and converting them into a digital form, according to an exemplary embodiment. The slides may be scanned with slide scanner 104, and the slide manager 105 may process the images on the slides into digitized pathology images and store the digitized images in storage 106.

The viewing application tool 108 refers to a process and system for providing a user (e.g., pathologist) with specimen property or image property information pertaining to digital pathology image(s), according to an exemplary embodiment. The information may be provided through various output interfaces (e.g., a screen, a monitor, a storage device, and/or a web browser, etc.).

The slide analysis tool 101, and each of its components, may transmit and/or receive digitized slide images and/or patient information to server systems 110, physician servers 121, hospital servers 122, clinical trial servers 123, research lab servers 124, and/or laboratory information systems 125 over an electronic network 120. Further, server systems 110 may include storage devices for storing images and data received from at least one of the slide analysis tool 101, the data ingestion tool 102, the slide intake tool 103, the slide scanner 104, the slide manager 105, and viewing application tool 108. Server systems 110 may also include processing devices for processing images and data stored in the storage devices. Server systems 110 may further include one or more machine learning tool(s) or capabilities, e.g., due to the processing devices. Alternatively or in addition, the present disclosure (or portions of the system and methods of the present disclosure) may be performed on a local processing device (e.g., a laptop).

Any of the above devices, tools, and modules may be located on a device that may be connected to an electronic network 120, such as the Internet or a cloud service provider, through one or more computers, servers, and/or handheld mobile devices.

Figure 1C:
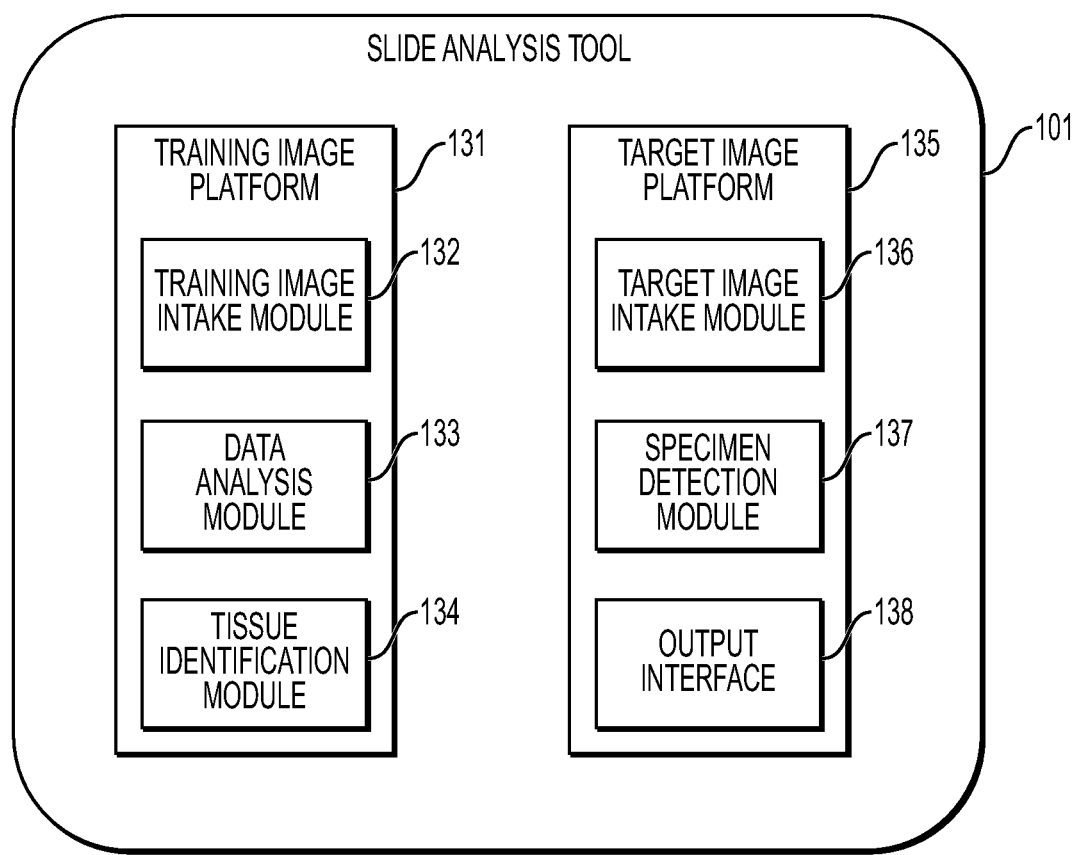
FIG. 1C illustrates an exemplary block diagram of a slide analysis tool, according to an exemplary embodiment of the present disclosure.

FIG. 1C illustrates an exemplary block diagram of a slide analysis tool 101, according to an exemplary embodiment of the present disclosure. The slide analysis tool 101 may include a training image platform 131 and/or a target image platform 135.

According to one embodiment, the training image platform 131 may include a training image intake module 132, a data analysis module 133, and a cell identification module 134.

The training image platform 131, according to one embodiment, may create or receive training images that are used to train a machine learning model to effectively analyze and classify digital pathology images. For example, the training images may be received from any one or any combination of the server systems 110, physician servers 121, hospital servers 122, clinical trial servers 123, research lab servers 124, and/or laboratory information systems 125. Images used for training may come from real sources (e.g., humans, animals, etc.) or may come from synthetic sources (e.g., graphics rendering engines, 3D models, etc.). Examples of digital pathology images may include (a) digitized slides stained with a variety of stains, such as (but not limited to) hematoxylin and eosin (H&E), Hematoxylin alone, IHC, molecular pathology, etc.; and/or (b) digitized tissue samples from a 3D imaging device, such as microCT.

The training image intake module 132 may create or receive a dataset comprising one or more training datasets corresponding to one or more health variables and/or one or more data variables. For example, the training datasets may be received from any one or any combination of the server systems 110, physician servers 121, hospital servers 122, clinical trial servers 123, research lab servers 124, and/or laboratory information systems 125. This dataset may be kept on a digital storage device. The data analysis module 133 may identify whether a set of individual cells belong to a cell of interest or a background of a digitized image. The cell identification module 134 may analyze digitized images and determine whether an individual cell in the cytology sample needs further analysis. It is useful to identify whether an individual cell needs further analysis and to aggregate these areas, and the identification of such may trigger an alert to a user.

According to one embodiment, the target image platform 135 may include a target image intake module 136, a specimen detection module 137, and an output interface 138. The target image platform 135 may receive a target image and apply the machine learning model to the received target image to determine a characteristic of a target data set. For example, the target data may be received from any one or any combination of the server systems 110, physician servers 121, hospital servers 122, clinical trial servers 123, research lab servers 124, and/or laboratory information systems 125. The target image intake module 136 may receive a target dataset corresponding to a target health variable or a data variable. Specimen detection module 137 may apply the machine learning model to the target dataset to determine a characteristic of the target health variable or a data variable. For example, the specimen detection module 137 may detect a trend of the target relationship. The specimen detection module 137 may also apply the machine learning model to the target dataset to determine a quality score for the target dataset. Further, the specimen detection module 137 may apply the machine learning model to the target images to determine whether a target element is present in a determined relationship.

The output interface 138 may be used to output information about the target data and the determined relationship. (e.g., to a screen, monitor, storage device, web browser, etc.).

Today, molecular laboratories may evaluate tumor genomes using tissue samples from unstained formalin fixed paraffin embedded tissue (FFPE) slides or blood using next-generation sequencing (NGS) to identify mutations, fusions, or deletions at the gene level. This evaluation may pinpoint the origin of the tumor, confer prognosis, guide treatment decisions (e.g., targeted therapies, immune-oncology therapies, or basket trials), and/or evaluate minimal residual disease (MRD). While this evaluation may be relatively straightforward for blood samples, it is a complex multi-step process for FFPE samples.

For FFPE, a current workflow may begin with a primary diagnosis of a tumor from either biopsy or resection slides by a pathologist. The tissue specimens from a patient may be embedded into FFPE blocks, a portion of each block may be sliced to prepare slides, and those slides may be used to render the diagnosis, leaving the remainder of the FFPE block to be potentially used for genomic sequencing.

After primary diagnosis, the treating oncologist may request either a pan-tumor or a specific genetic test. The request may be presented to the sign-out pathologist who re-reviews the slides from each FFPE block that contains the most suitable section(s) of tumor. To identify the most suitable tumor section(s), the block containing existing slides that have the highest tumor purity, least necrosis, and/or least inflammation may be chosen. This step may be performed via manual re-review of slides and may be quite time consuming. After identifying the block, eleven unstained slides from that block may be cut into the workflow for a pan-tumor NGS panel. The eleventh slide may then be stained with H&E and evaluated for residual tumor to ensure the previous ten unstained slides have sufficient quantity of tumor. These ten unstained slides may be sent to the molecular laboratory along with a requisition/form containing basic patient information (age, gender, topline diagnosis).

Upon arrival in the molecular lab, the first unstained slide may be stained with H&E and evaluated by a technician under a microscope for the precise location of the tumor. The tumor may be annotated by the technician using either a diamond tipped pencil or a marker. This location may be roughly marked on the remaining nine unstained slides such that a technician can "macro dissect" these areas rich in tumor from the slide. Macro dissection involves using a blade to scrape the unstained FFPE tissue from the surface of the slide and suctioning it up such that the tissue can be macerated and DNA extracted. Polymerase chain reaction (PCR) testing may then be performed on those tumor sections, and the results may be fed through a robust bioinformatics data pipeline. A molecular pathologist may analyze the results and classify mutations into various tiers of clinical significance and action.

If there is sufficient tumor for molecular testing, then the molecular test may be performed on the sample after being received by a lab. The lab may generate a comprehensive report that is sent back to the primary diagnosing pathologist, and this report may be appended to the original diagnostic report for subsequent review by the oncologist. This process may take two weeks, but it can take longer if there is insufficient tumor, in which case another two weeks may be needed.

Using AI to Identify the Quality of One or More Slides from an FFPE Block for Additional Testing (e.g., Applying a Molecular/Genomic Test)

Systems and methods of the present disclosure may facilitate selecting a highest quality FFPE block by using artificial intelligence (AI) to provide a quality score Q for each FFPE block based on the information available about each block. The quality score Q may be indicative of a quality (e.g., percentage of tumor content, tumor purity, necrosis content, etc.) of each block and may be used to determine the best or appropriate block for additional testing. Various ways to determine the quality score Q are described in more detail hereinafter. The quality and/or quality score Q of the block may depend on percentage of tumor content, tumor purity, necrosis content, etc. The AI system and/or a pathologist may then select the block with the highest quality. The AI system may also facilitate a verification process of ensuring that the block is of sufficient quality by assessing a quality of a final (e.g., $11^{th}$) slide in each block and determining whether the quality of that slide meets a quality and/or quantity threshold and/or selecting a new block when the slide does not meet the quality and/or quantity threshold.

Figure 2:
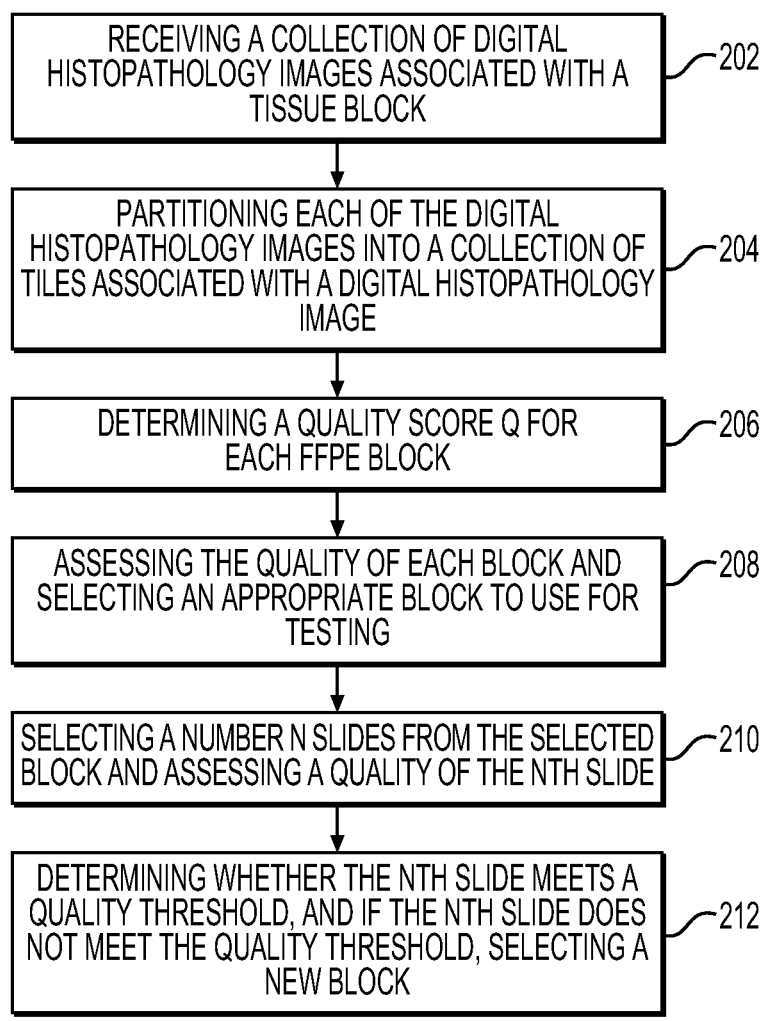
FIG. 2 is a flowchart illustrating a method of verifying slide and block quality for testing, according to an exemplary embodiment of the present disclosure.

FIG. 2 is a flowchart illustrating an exemplary method for verifying slide and block quality for testing, according to an exemplary embodiment of the present disclosure. For example, an exemplary method 200 (e.g., steps 202-212) may be performed by slide analysis tool 101 automatically or in response to a request from a user.

In step 202, the method may include receiving a collection of digital histopathology images associated with a tissue block at an electronic storage device (e.g. hard drive, network drive, cloud storage, system memory, etc.).

In step 204, the method may include partitioning each of the digital histopathology images into a collection of tiles associated with a digital histopathology image.

In step 206, the method may include providing or determining a quality score Q for each FFPE block based on the information available about each block. A quality of each FFPE block may depend on percentage of tumor content, tumor purity, necrosis content, etc. Determining the quality score Q may be performed using an AI system that can measure attributes such as these from all slides prepared from each block and can then determine a quality metric for each slide in the block based on the measured attributes. The AI system may run on the slides from each block and output the quality score Q for each block. The AI system may also be configured to prioritize or rank the blocks based on the determined quality score Qs.

In step 208, the method may include assessing the quality of each block, based on the quality score Q, and choosing or selecting an appropriate block to use for testing. For example, choosing the appropriate block to use for testing may include choosing the block with the highest quality score Q or choosing the block with the quality score Q that indicates the highest quality across slides. This assessment and/or selection may be performed by a user (e.g., a pathologist assessing the output quality scores Q) or alternatively using the AI system.

For example, selection of a tumor block may be performed by a sign-out pathologist, whose criteria for optimal block selection may include tumor quantity and quality (i.e., least biopsy site change, inflammation, etc.). An algorithm designed or configured to detect a tumor and to quantify a tumor may be complimented by an algorithm that detects a block of tumor most likely to result in a positive molecular finding.

In step 210, the method may include selecting or preparing a number N slides from the selected block and assessing a quality of the $N^{th}$ or final slide (e.g., $11^{th}$ slide). This assessment may be performed by the AI system. Alternatively, N slides may be prepared from the selected block, and the Nth or last slide (e.g, N=11) may be stained, for example with H&E, to verify that the block is of sufficient quality. Alternatively, the N−1 slide may be stained. This verification may include a manual inspection.

In step 212, the method may include determining whether the Nth slide meets a quality threshold. If the Nth slide does not meet the quality threshold, the method may include selecting a new block for assessment.

During step 206 of assessing a quality Q score and/or during 210 of assessing the quality of the Nth slide, a quality assessment system may be described by a function Q(I1, I2, . . . , IN, C), where the function may output a number indicating a quality. Higher values may indicate higher quality. Each IN may be a digital image of the slide in the block. C may describe any specific constraints, e.g., "Do not select blocks with more than p % necrosis," or C may describe a weighting to use for each of the relevant variables for quality, e.g., quality is a weighted sum of various measurements such as percentage of necrosis. There may be multiple approaches to creating Q.

Using an AI System that Infers Attributes

An AI system may infer a number N attributes vi, such as a percentage of necrosis as v1, a percentage of tumor as v2, etc. After computing those attributes vi, the attributes vi be integrated in a linear or nonlinear manner to produce a quality score Q for the block.

Figure 3A:
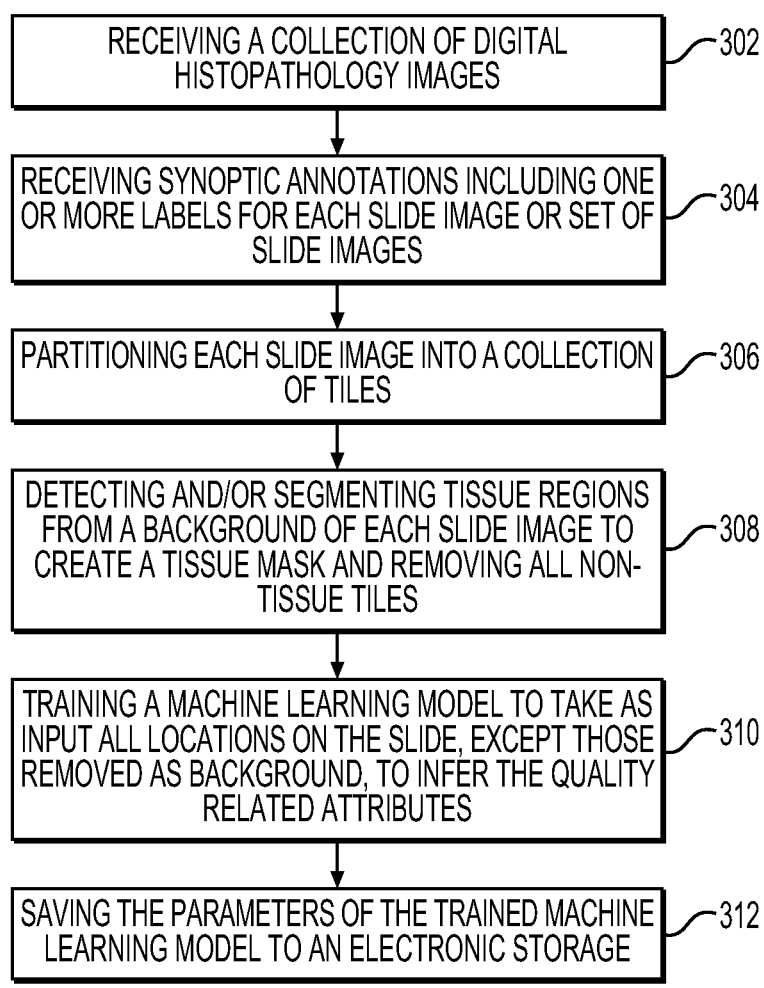
FIGS. 3A and 3B are flowcharts illustrating a method of training and using a machine learning model to output a quality score function, according to an exemplary embodiment of the present disclosure.
Figure 3B:
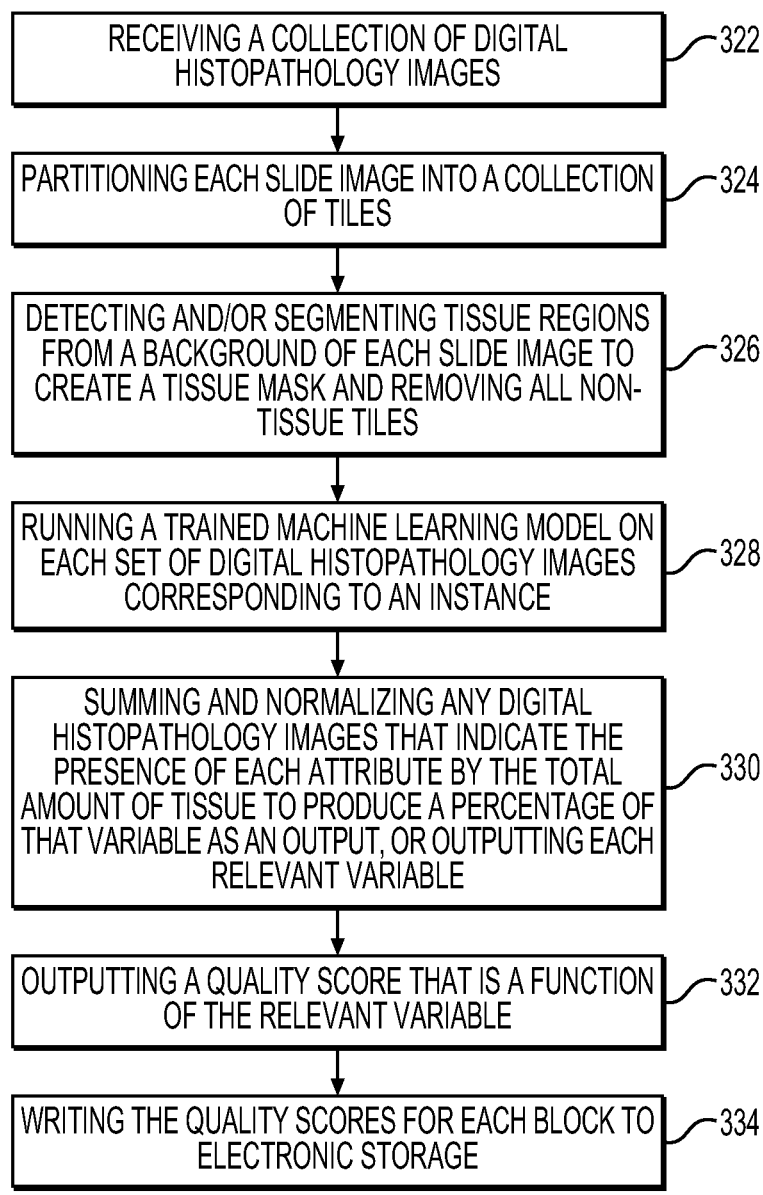

FIGS. 3A and 3B are flowcharts illustrating an exemplary method for verifying slide and block quality for testing, according to an exemplary embodiment of the present disclosure. For example, an exemplary method 300 (e.g., steps 302-312), shown in FIG. 3A, or exemplary method 320 (e.g., steps 322-334), shown in FIG. 3B may be performed by slide analysis tool 101 automatically or in response to a request from a user.

In step 302, the method may include receiving a collection of digital histopathology images into a digital storage device (e.g., hard drive, network drive, cloud storage, RAM, etc.).

In step 304, the method may include receiving synoptic annotations including one or more labels for each slide image or set of slide images. These labels may be at the pixel-level, tile-level, slide-level, or part specimen-level. The labels may be binary (or multi-label binary), categorical, ordinal, or real-valued. These variables may describe the presence of quality-related attributes, e.g., invasive cancer, necrosis present and/or percentage, etc.

In step 306, the method may include partitioning each slide image into a collection of tiles.

In step 308, the method may include detecting and/or segmenting tissue regions from a background of each slide image to create a tissue mask and removing all non-tissue tiles. This could be done in a variety of ways, including but not limited to:
  a. Thresholding based methods, e.g., based on color/ intensity, based on texture features, Otsu's method, etc., followed by running the connected components algorithm
  b. Segmentation algorithms, e.g., k-means, graph cuts, Mask R-CNN, etc.

In step 310, the method may include training a machine learning model to take as input all locations on the slide, except those removed as background, to infer the quality related attributes. The model may be a support-vector machine (SVM), convolutional neural network (CNN), recurrent neural network (RNN), Transformer, Graph Neural Network, multilayer perceptron (MLP), Relationship network, etc. The system may be trained to produce an image for each relevant attribute, e.g., a binary image indicating where necrosis is found, or it may be trained to directly output the amount of the relevant variable present, e.g., a number indicating the percentage of necrosis, another number indicating the tumor purity, or whether the there is an amount of the relevant variable, such as tumor tissue, beyond a predetermined threshold, etc.

In step 312, the method may include saving the parameters of the trained machine learning model to an electronic storage.

Referring to FIG. 3B, in step 322, the method may include receiving a collection of digital histopathology images at a digital storage device (e.g., hard drive, network drive, cloud storage, RAM, etc.).

In step 324, the method may include partitioning each slide image into a collection of tiles.

In step 326, the method may include detecting and/or segmenting tissue regions from a background of each slide image to create a tissue mask and removing all non-tissue tiles. This could be done in a variety of ways, including but not limited to:
  a. Thresholding based methods, e.g., based on color/ intensity, based on texture features, Otsu's method, etc., followed by running the connected components algorithm
  b. Segmentation algorithms, e.g., k-means, graph cuts, Mask R-CNN, etc.

In step 328, the method may include running a trained machine learning model on each set of digital histopathology images corresponding to an instance.

In step 330, the method may include summing and normalizing any digital histopathology images that indicate the presence of each attribute by the total amount of tissue to produce a percentage of that variable as an output, or outputting each relevant variable. It may be determined if the total amount of tissue meets or exceeds a predetermined threshold. The system may be trained to produce "images" that indicate the presence of each attribute, e.g., an image that indicates where necrosis is found. Alternatively, the system could instead be trained to directly output each relevant variable, where the $i^{th}$ relevant variable may be indicated by $v_i$.

In step 332, the method may include outputting a quality score that is a function of the relevant variable, either as a linear or nonlinear function. This function may be a linear combination specified by values in the configuration C, e.g., the output Q may be equal to $w_1v_1+w_2v_2+, \ldots, +w_Nv_N$ where n is the total number of relevant variables. This score could also be nonlinear, e.g., if necrosis is greater than p % then the quality is 0 otherwise it is a linear combination specified by the configuration C given by $w_1v_1+w_2v_2+, \ldots, +w_Nv_N$.

In step 334, the method may include writing the quality scores for each block to electronic storage.

Using a System that Learns Quality Directly.

This approach uses an AI system that directly infers if the slides in a block are adequate for testing or if the slides in the block will not suffice, without necessarily producing intermediate variables.

Figure 4A:
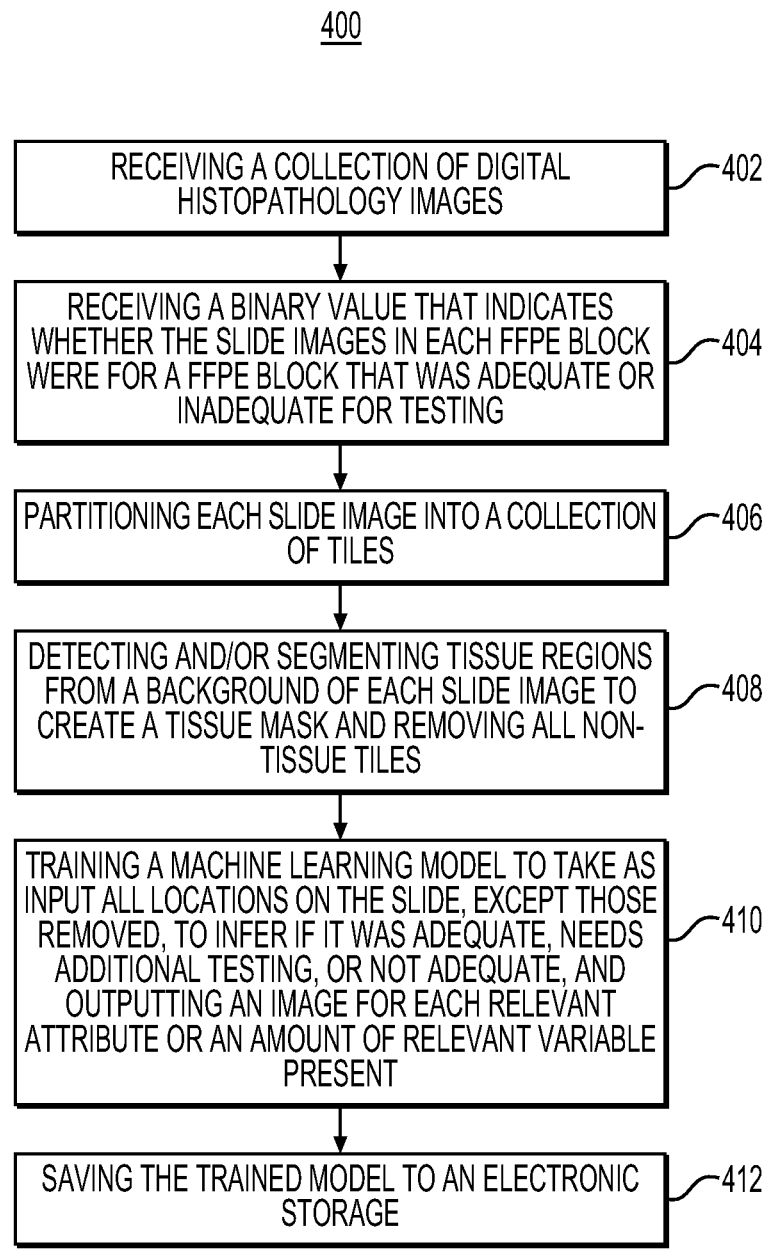
FIGS. 4A and 4B are flowcharts illustrating a method of training and using a machine learning model to determine whether a formalin fixed paraffin embedded tissue (FFPE) block should have additional slides prepared for testing, according to an exemplary embodiment of the present disclosure.
Figure 4B:
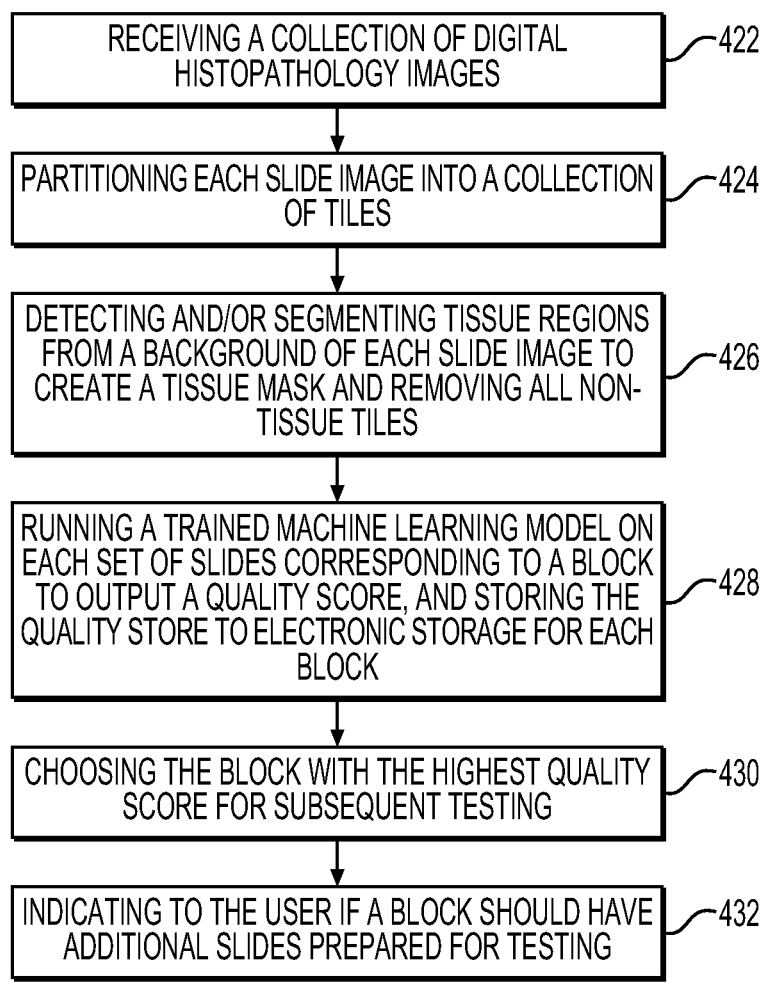

FIGS. 4A and 4B are flowcharts illustrating an exemplary method for verifying slide and block quality for testing, according to an exemplary embodiment of the present disclosure. For example, an exemplary method 400 (e.g., steps 402-412) shown in FIG. 4A or exemplary method 420 (e.g., steps 422-434) shown in FIG. 4B may be performed by slide analysis tool 101 automatically or in response to a request from a user.

In step 402, the method may include receiving a collection of digital histopathology images into a digital storage device (e.g., hard drive, network drive, cloud storage, RAM, etc.).

In step 404, the method may include receiving a binary value that indicates whether the slide images in each FFPE block were for a FFPE block that was adequate or inadequate for testing.

In step 406, the method may include partitioning each slide image into a collection of tiles.

In step 408, the method may include detecting and/or segmenting tissue regions from a background of each slide image to create a tissue mask and removing all non-tissue tiles. This could be done in a variety of ways, including but not limited to:
  a. Thresholding based methods, e.g., based on color/intensity, based on texture features, Otsu's method, etc., followed by running the connected components algorithm
  b. Segmentation algorithms, e.g., k-means, graph cuts, Mask R-CNN, etc.

In step 410, the method may include training a machine learning model to take as input all locations on the slide, except those removed, to infer if it was adequate, needs additional testing, or not adequate, and outputting an image for each relevant attribute or an amount of relevant variable present. The model may be a support vector machine (SVM), convolutional neural network (CNN), recurrent neural network (RNN), Transformer, Graph Neural Network, multilayer perceptron (MLP), Relationship network, Semantic Segmentation network, Instance Segmentation network (e.g., Mask R-CNN), object detection CNN (e.g., Faster R-CNN), etc. The system may be trained to produce an image for each relevant attribute, e.g., a binary image indicating where necrosis is found, or it may be trained to directly output the amount of the relevant variable present, e.g., a number indicating the percentage of necrosis, another number indicating the tumor purity, etc.

In step 412, the method may include saving the trained model to an electronic storage.

In step 422, the method may include receiving a collection of digital histopathology images into a digital storage device (e.g., hard drive, network drive, cloud storage, RAM, etc.).

In step 424, the method may include partitioning each slide image into a collection of tiles.

In step 426, the method may include detecting and/or segmenting tissue regions from a background of each slide image to create a tissue mask and removing all non-tissue tiles. This could be done in a variety of ways, including but not limited to:
  a. Thresholding based methods, e.g., based on color/intensity, based on texture features, Otsu's method, etc., followed by running the connected components algorithm
  b. Segmentation algorithms, e.g., k-means, graph cuts, Mask R-CNN, etc.

In step 428, the method may include running a trained machine learning model on each set of slides corresponding to a block to output a quality score, and storing the quality store to electronic storage for each block.

In step 430, the method may include choosing the block with the highest quality score for subsequent testing. This may be done manually by the user, or automatically by slide analysis tool 101.

Figure 5A:
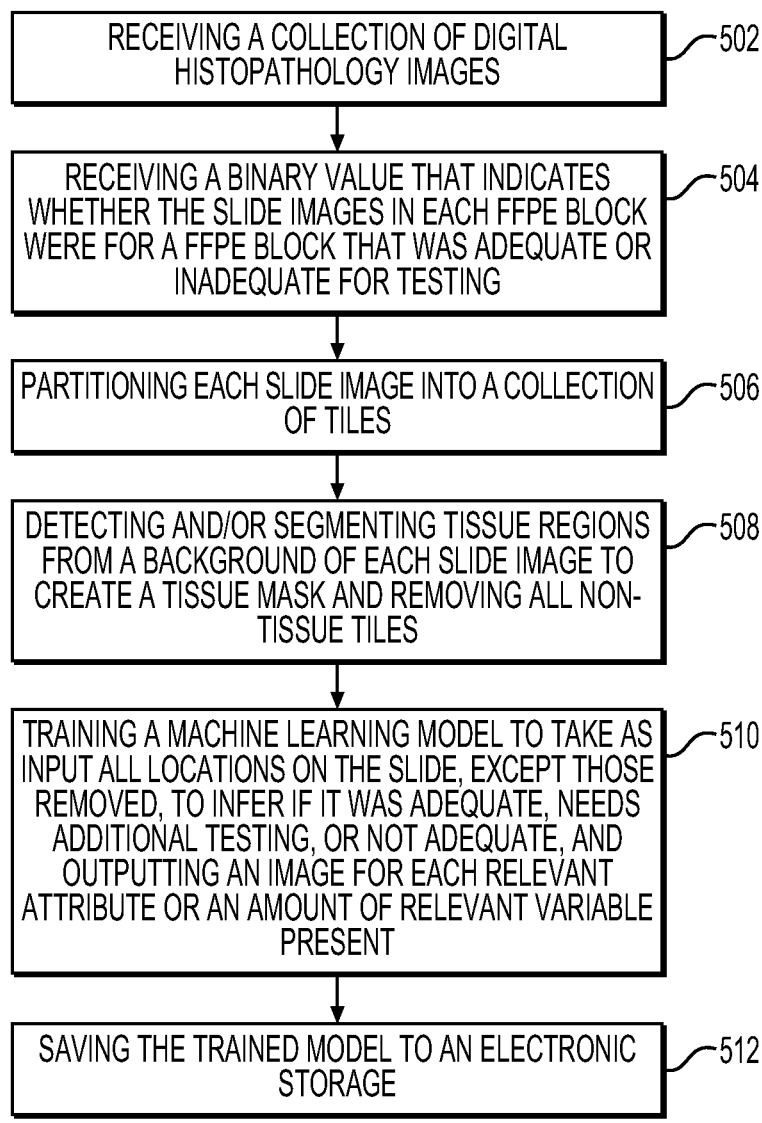
FIGS. 5A and 5B are flowcharts illustrating a method of training and using a machine learning model to determine if a new FFPE block of tissues should be prepared for testing, according to an exemplary embodiment of the present disclosure.
Figure 5B:
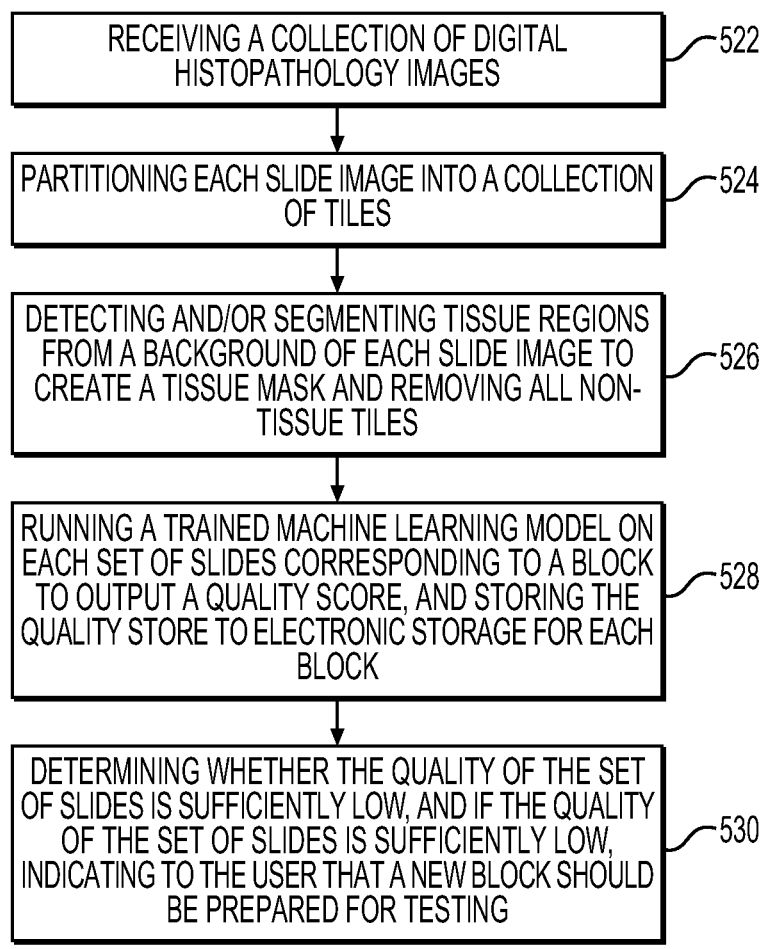

In step 432, the method may include indicating to the user if a block should have additional slides prepared for testing. For Use Verifying the Final Slide from the Chosen Block has Adequate Quality:

FIGS. 5A and 5B are flowcharts illustrating an exemplary method for verifying slide and block quality for testing, according to an exemplary embodiment of the present disclosure. For example, an exemplary method 500 (e.g., steps 502-512) shown in FIG. 5A or exemplary method 520 (e.g., steps 522-534) shown in FIG. 5B may be performed by slide analysis tool 101 automatically or in response to a request from a user.

In step 502, the method may include receiving a collection of digital histopathology images into a digital storage device (e.g., hard drive, network drive, cloud storage, RAM, etc.).

In step 504, the method may include receiving a binary value that indicates whether the slide images in each FFPE block were for a FFPE block that was adequate or inadequate for testing.

In step 506, the method may include partitioning each slide image into a collection of tiles.

In step 508, the method may include detecting and/or segmenting tissue regions from a background of each slide image to create a tissue mask and removing all non-tissue tiles. This could be done in a variety of ways, including but not limited to:
  a. Thresholding based methods, e.g., based on color/intensity, based on texture features, Otsu's method, etc., followed by running the connected components algorithm
  b. Segmentation algorithms, e.g., k-means, graph cuts, Mask R-CNN, etc.

In step 510, the method may include training a machine learning model to take as input all locations on the slide, except those removed, to infer if it was adequate, needs additional testing, or not adequate, and outputting an image for each relevant attribute or an amount of relevant variable present. The model may be a SVM, CNN, RNN, Transformer, Graph Neural Network, MLP, Relationship network, Semantic Segmentation network, Instance Segmentation network (e.g., Mask R-CNN), object detection CNN (e.g., Faster R-CNN), etc. The system may be trained to produce an image for each relevant attribute, e.g., a binary image indicating where necrosis is found, or it may be trained to directly output the amount of the relevant variable present, e.g., a number indicating the percentage of necrosis, another number indicating the tumor purity, etc.

In step 512, the method may include saving the trained model to an electronic storage.

In step 522, the method may include receiving a collection of digital histopathology images into a digital storage device (e.g., hard drive, network drive, cloud storage, RAM, etc.).

In step 524, the method may include partitioning each slide image into a collection of tiles.

In step 526, the method may include detecting and/or segmenting tissue regions from a background of each slide image to create a tissue mask and removing all non-tissue tiles. This could be done in a variety of ways, including but not limited to:
  a. Thresholding based methods, e.g., based on color/intensity, based on texture features, Otsu's method, etc., followed by running the connected components algorithm
  b. Segmentation algorithms, e.g., k-means, graph cuts, Mask R-CNN, etc.

In step 528, the method may include running a trained machine learning model on each set of slides corresponding to a block to output a quality score, and storing the quality store to electronic storage for each block.

In step 530, the method may include determining whether the quality of the set of slides is sufficiently low (e.g., less than a predetermined quality), and if the quality of the set of slides is sufficiently low, indicating to the user that a new block should be prepared for testing.

Figure 6:
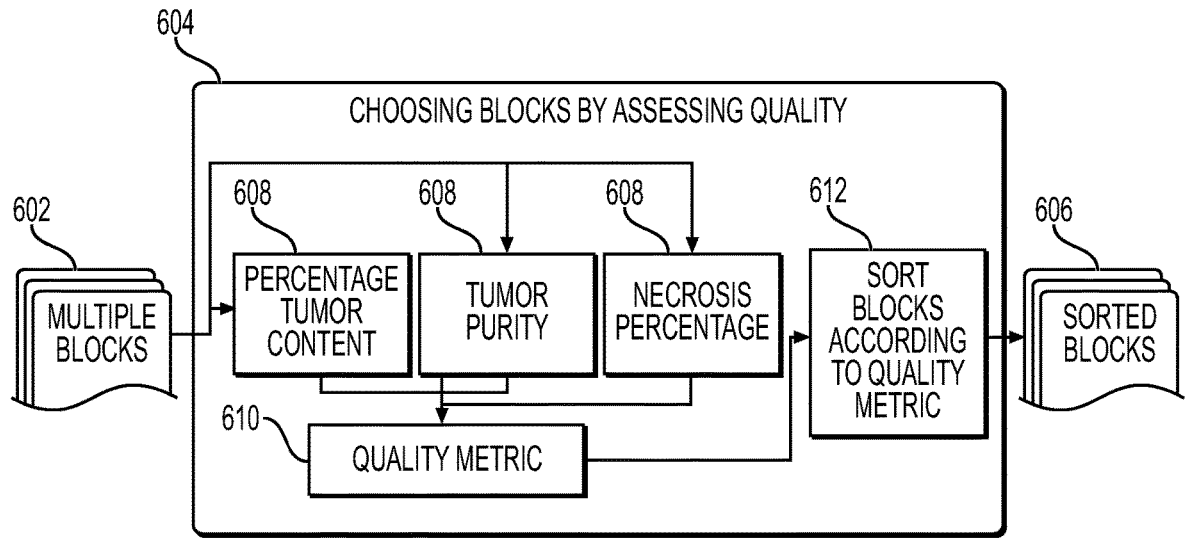
FIG. 6 is an exemplary use of the machine learning model to assess block quality, according to an exemplary embodiment of the present disclosure.

FIG. 6 is an exemplary use of the machine learning model to assess block quality. The machine learning model 604 may have an input 602. In the exemplary illustration, the input 602 is represented by multiple tissue blocks. The input 602 is analyzed for quality by the machine learning model 604 using variables 608 (for example, percentage tumor content, tumor purity, and/or necrosis percentage), but a different number of variables may be used. A quality metric 610 may be output from the analysis using variables 608, and then may be used to sort the input 602 (blocks) in step 612. The output 606 may be the blocks sorted in step 612.

Continuous Recurrence Score for Invasive Breast Cancer

After invasive breast cancer is detected, a genomic assay of the tumor may be performed to determine whether to forgo additional treatment, to give the patient endocrine (hormone) therapy, to give the patient adjuvant chemotherapy, or some other therapy. These tests may assess the risk of recurrence and metastasis of disease after excising the primary tumor using a continuous scoring system. Additionally, tests may look at genomic information relating to proliferation, invasion, metastasis, stromal integrity, and angiogenesis.

For example, the EndoPredict (EPclin) test is based on ribonucleic acid (RNA) expression of 12 genes, and combines this genomic information with additional clinical features to predict the ten-year distant recurrence (DR) rate. A score between 1 and 6, with 6 indicating a high risk and 1 indicting a low risk, may be assigned to the input tissue. Another example test is MammaPrint, which is a 70-gene assay that uses formalin-fixed-paraffin-embedded (FFPE) or fresh tissue. RNA from the tumor sample is isolated and used to predict a continuous score, with values greater than 0 indicating low risk of cancer recurrence and values less than 0 indicating a higher risk of recurrence, which suggests that adjuvant chemotherapy may be needed.

Another example test is the Breast Cancer Index (BCI) test, which analyzes seven genes to predict cancer recurrence. Two scores are output: the BCI Prognostic score estimates the likelihood of the cancer returning five to ten years after diagnosis on a continuous scale of 0 to 10, with a score of 5.1 to 10 indicating a high risk of recurrence. The BCI Predictive score estimates the likelihood of benefit from taking endocrine therapy for five additional years, for ten years total of endocrine therapy.

Oncotype DX Recurrence Score is another such assay, which looks at the expression of 21 genes within a tumor. An output number between 0 to 100 indicates the risk of cancer recurrence, with a score of greater than 31 indicating a high risk of metastasis and the need for adjuvant chemotherapy with endocrine therapy, a score of 26 to 30 indicating uncertain benefit for adjuvant chemotherapy when used with endocrine therapy, and a score less than 26 indicating that endocrine therapy alone could suffice for treatment after surgery.

The Prosigna Breast Cancer Prognostic Gene Signature Assay (i.e., the PAM50 gene signature) uses RNA from FFPE samples to estimate the risk of distant recurrence for hormone receptor positive breast cancer. A continuous score from 0 to 100 is produced, with a higher score indicating a greater risk of recurrence to guide treatment decisions.

All of these tests may require selection of an appropriate block, confirmation that the unstained slides from that block have adequate tumor tissue, and determination of the location of the tumor in the slides before the application of the genomic assay. Using current techniques, these steps are manual, time-consuming, and error prone. Techniques presented herein may select and verify high-quality slides with sufficient tumor content for genomic testing. Techniques presented herein may involve automatic, quicker, and more accurate steps than in current techniques.

Continuous Score for Recurrence of Non-Invasive Breast Cancer

Following diagnosis of non-invasive breast cancer, adjuvant treatment may be necessary after a patient has a lumpectomy or mastectomy. This treatment may include endocrine therapy or radiation treatment to reduce the risk recurrence, but these treatments have negative side effects. To determine the benefit a patient may have from these treatments, genomic assays have been developed.

The most common form of non-invasive breast cancer is ductal carcinoma in situ (DCIS). Today, the primary genomic test for determining treatment options for DCIS is Oncotype DX DCIS, which is a 12-panel genomic test. This test produces a continuous score from 0 to 100 to determine the risk of breast cancer recurrence, with higher values indicating greater need for adjuvant treatment to prevent recurrence.

Systems and methods of the present disclosure may be used to select and verify high-quality slides with sufficient tumor content for genomic testing.

Workflow for Continuous Score for Prostate Cancer Treatment Recommendation

To diagnose prostate cancer, men may receive a prostate biopsy. The biopsy sample may then be processed and visually reviewed by a pathologist to determine the presence and severity of disease. However, prostate cancer treatments, e.g., removal of the prostate, hormone therapy, and/or radiation therapy, may have a negative impact on a man's quality of life, and some patients may not need aggressive treatment.

An alternative to only using pathologic assessment of prostate tissue samples is to predict tumor aggressiveness using genomic assays. For example, the Oncotype DX Genomic Prostate Score looks at 17 genes to determine prostate cancer aggressiveness on a continuous score from 0 to 100. Patients with values closer to 0 could have active surveillance recommended, whereas patients with higher scores should have immediate, aggressive treatment to reduce the risk of an adverse outcome (e.g., death or metastasis). Another test is the Prolaris assay, which combines genomic assessment with other measurements to determine a continuous score, where a higher score indicates the aggressiveness of the cancer. This test may help determine whether a man can choose active surveillance for prostate cancer instead of aggressive treatment.

Systems and methods of the present disclosure may be used to select and verify high-quality slides with sufficient tumor content for genomic testing.

Workflow for Continuous Scores for Likelihood of Malignancy

A tumor is an abnormal mass of cells, which can be benign or malignant. A benign tumor lacks the ability to metastasize or invade surrounding tissue, whereas a malignant tumor has that ability. In some situations, pathological assessment does not suffice for determining if a tumor is malignant or benign. In these types of scenarios, a continuous score may be used to facilitate the determination.

For example, the Myriad myPath Melanoma test measures 23 genes associated with cell differentiation, cell signaling, and immune response signaling to produce a continuous score on a scale of approximately −16 to 10, with scores greater than zero indicating the skin tumor is likely malignant and that aggressive treatment is needed, and scores of less than −2 indicating the tumor is likely benign.

Systems and methods of the present disclosure may be used to select and verify high-quality slides with sufficient tumor content for genomic testing.

Figure 7:
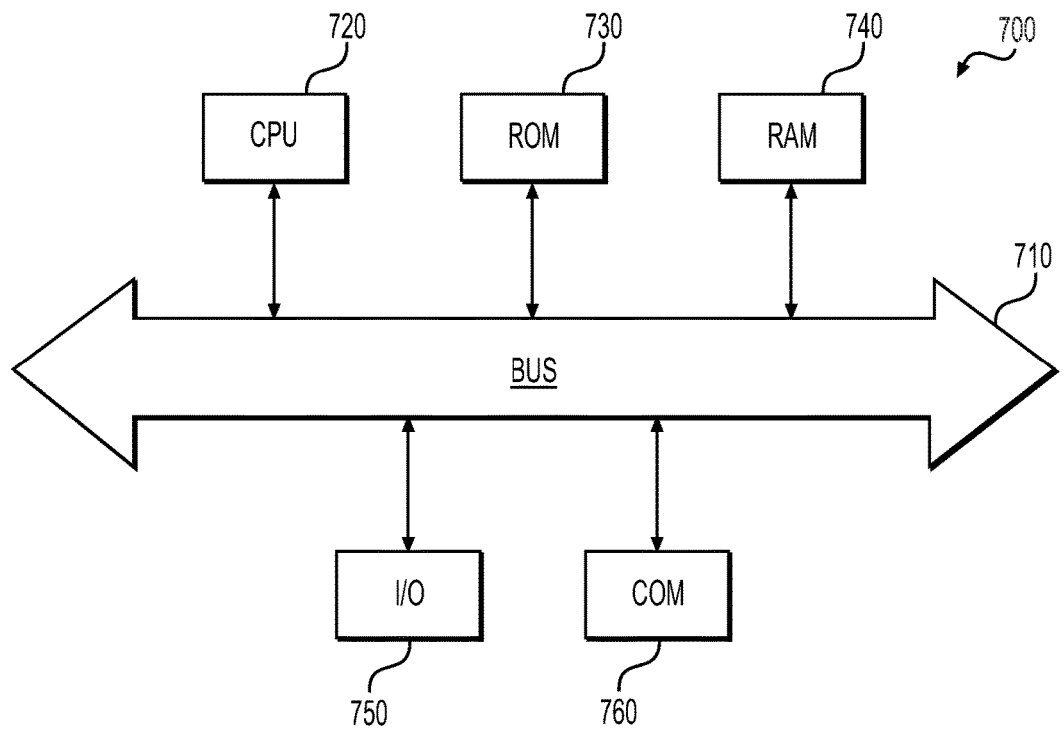
FIG. 7 depicts an example system that may execute techniques presented herein.

As shown in FIG. 7, device 700 may include a central processing unit (CPU) 720. CPU 720 may be any type of processor device including, for example, any type of special purpose or a general-purpose microprocessor device. As will be appreciated by persons skilled in the relevant art, CPU 720 also may be a single processor in a multi-core/multi-processor system, such system operating alone, or in a cluster of computing devices operating in a cluster or server farm. CPU 720 may be connected to a data communication infrastructure 710, for example a bus, message queue, network, or multi-core message-passing scheme.

Device 700 may also include a main memory 740, for example, random access memory (RAM), and also may include a secondary memory 730. Secondary memory 730, e.g. a read-only memory (ROM), may be, for example, a hard disk drive or a removable storage drive. Such a removable storage drive may comprise, for example, a floppy disk drive, a magnetic tape drive, an optical disk drive, a flash memory, or the like. The removable storage drive in this example reads from and/or writes to a removable storage unit in a well-known manner. The removable storage may comprise a floppy disk, magnetic tape, optical disk, etc., which is read by and written to by the removable storage drive. As will be appreciated by persons skilled in the relevant art, such a removable storage unit generally includes a computer usable storage medium having stored therein computer software and/or data.

In alternative implementations, secondary memory 730 may include similar means for allowing computer programs or other instructions to be loaded into device 700. Examples of such means may include a program cartridge and cartridge interface (such as that found in video game devices), a removable memory chip (such as an EPROM or PROM) and associated socket, and other removable storage units and interfaces, which allow software and data to be transferred from a removable storage unit to device 700.

Device 700 also may include a communications interface ("COM") 760. Communications interface 760 allows software and data to be transferred between device 700 and external devices. Communications interface 760 may include a modem, a network interface (such as an Ethernet card), a communications port, a PCMCIA slot and card, or the like. Software and data transferred via communications interface 760 may be in the form of signals, which may be electronic, electromagnetic, optical or other signals capable of being received by communications interface 760. These signals may be provided to communications interface 760 via a communications path of device 700, which may be implemented using, for example, wire or cable, fiber optics, a phone line, a cellular phone link, an RF link or other communications channels.

The hardware elements, operating systems, and programming languages of such equipment are conventional in nature, and it is presumed that those skilled in the art are adequately familiar therewith. Device 700 may also include input and output ports 750 to connect with input and output devices such as keyboards, mice, touchscreens, monitors, displays, etc. Of course, the various server functions may be implemented in a distributed fashion on a number of similar platforms, to distribute the processing load. Alternatively, the servers may be implemented by appropriate programming of one computer hardware platform.

Throughout this disclosure, references to components or modules generally refer to items that logically can be grouped together to perform a function or group of related functions. Like reference numerals are generally intended to refer to the same or similar components. Components and modules may be implemented in software, hardware or a combination of software and hardware.

The tools, modules, and functions described above may be performed by one or more processors. "Storage" type media may include any or all of the tangible memory of the computers, processors, or the like, or associated modules thereof, such as various semiconductor memories, tape drives, disk drives and the like, which may provide non-transitory storage at any time for software programming.

Software may be communicated through the Internet, a cloud service provider, or other telecommunication networks. For example, communications may enable loading software from one computer or processor into another. As used herein, unless restricted to non-transitory, tangible "storage" media, terms such as computer or machine "readable medium" refer to any medium that participates in providing instructions to a processor for execution.

The foregoing general description is exemplary and explanatory only, and not restrictive of the disclosure. Other embodiments of the invention will be apparent to those skilled in the art from consideration of the specification and practice of the invention disclosed herein. It is intended that the specification and examples to be considered as exemplary only.

What is claimed is:

1. A computer-implemented method for verifying slide and block quality for testing, the method comprising:
    receiving a collection of one or more digital images, the collection associated with a tissue block and corresponding to an instance, at a digital storage device;
    applying a machine learning model to the collection to identify a presence or an absence of necrosis in the tissue block from a digital image in the collection;
    determining an amount or a percentage of tissue with necrosis from the digital image in the collection that indicates the presence of necrosis; and
    outputting a quality score corresponding to the determined amount or percentage of tissue with necrosis being below a predetermined value, wherein the quality score is equal to zero when the determined amount or percentage of tissue with necrosis is greater than the predetermined value and the quality score is a linear combination of two or more attribute values when the determined amount or percentage of tissue with necrosis is less than or equal to the predetermined value.

2. The computer-implemented method of claim 1, wherein determining the amount or percentage includes summing and normalizing the digital image in the collection that indicates the presence of the necrosis or tumor by a total amount of tissue.

3. The computer-implemented method of claim 1, further comprising:
    partitioning each digital image of the collection of digital images into a collection of tiles;
    detecting and/or segmenting a tissue region from a background of the digital image to create a tissue mask; and
    removing all tiles in the collection of tiles that comprise the background.

4. The computer-implemented method of claim 3, wherein detecting and/or segmenting comprises using one or more thresholding-based methods and running a connected components algorithm.

5. The computer-implemented method of claim 3, wherein detecting and/or segmenting comprises using one or more segmentation algorithms.

6. The computer-implemented method of claim 1, further comprising:
determining a tissue block with a highest quality score for subsequent testing.

7. The computer-implemented method of claim 6, further comprising:
indicating to a user that the tissue block has at least one additional slide to prepare for testing.

8. The computer-implemented method of claim 6, further comprising:
determining whether the quality score is sufficiently low.

9. The computer-implemented method of claim 8, further comprising:
indicating to a user to prepare a new block for testing when the quality score is determined to be sufficiently low.

10. The computer-implemented method of claim 1, further comprising:
outputting a function of at least one variable corresponding to the quality score.

11. The computer-implemented method of claim 10, wherein the function of the at least one variable is a linear function.

12. The computer-implemented method of claim 10, wherein the function of the at least one variable is a nonlinear function.

13. The computer-implemented method of claim 1, further comprising:
outputting a binary image indicating where the necrosis or tumor is located.

14. The computer-implemented method of claim 1, further comprising:
receiving a synoptic annotation comprising one or more label for each digital image.

15. The computer-implemented method of claim 14, wherein the one or more label is a pixel-level label, a tile level label, a slide-level label, and/or a part specimen-level label.

16. The computer-implemented method of claim 1, wherein the digital image is a digital histopathology image.

17. A system for using a machine learning model to verify slide and block quality for testing, the system comprising:
at least one memory storing instructions; and
at least one processor configured to execute the instructions to perform operations comprising:
receiving a collection of one or more digital images, the collection associated with a tissue block and corresponding to an instance, at a digital storage device;
applying a machine learning model to the collection to identify a presence or an absence of necrosis in the tissue block from a digital image in the collection;
determining an amount or a percentage of tissue with necrosis from the digital image in the collection that indicates the presence of necrosis; and
outputting a quality score corresponding to the determined amount or percentage of tissue with necrosis being below a predetermined value, wherein the quality score is equal to zero when the determined amount or percentage of tissue with necrosis is greater than the predetermined value and the quality score is a linear combination of two or more attribute values when the determined amount or percentage of tissue with necrosis is less than or equal to the predetermined value.

18. The system of claim 17, wherein determining the amount or percentage includes summing and normalizing the digital image in the collection that indicates the presence of the necrosis or cancer by a total amount of tissue.

19. A non-transitory computer-readable medium storing instructions that, when executed by a processor, perform a method of using a machine learning model to verify slide and block quality for testing, the method comprising:
receiving a collection of one or more digital images, the collection associated with a tissue block and corresponding to an instance, at a digital storage device;
applying a machine learning model to the collection to identify a presence or an absence of necrosis in the tissue block from a digital image in the collection;
determining an amount or a percentage of tissue with necrosis from the digital image in the collection that indicates the presence of necrosis; and
outputting a quality score corresponding to the determined amount or percentage of tissue with necrosis being below a predetermined value, wherein the quality score is equal to zero when the determined amount or percentage of tissue with necrosis is greater than the predetermined value and the quality score is a linear combination of two or more attribute values when the determined amount or percentage of tissue with necrosis is less than or equal to the predetermined value.

20. The method of claim 19, wherein the method further comprises:
partitioning each digital image of the collection of digital images into a collection of tiles;
detecting and/or segmenting a tissue region from a background of the digital image to create a tissue mask; and
removing all tiles in the collection of tiles that comprise the background.

* * * * *